United States Patent
Amplatz et al.

[11] Patent Number: 5,944,738
[45] Date of Patent: Aug. 31, 1999

[54] PERCUTANEOUS CATHETER DIRECTED CONSTRICTING OCCLUSION DEVICE

[75] Inventors: Kurt Amplatz, St. Paul; Michael R. Afremov, St. Louis Park, both of Minn.

[73] Assignee: AGA Medical Corporation, Golden Valley, Minn.

[21] Appl. No.: 09/019,620

[22] Filed: Feb. 6, 1998

[51] Int. Cl.$^6$ .................................................. A61B 17/08
[52] U.S. Cl. ............................................................ 606/213
[58] Field of Search ................................... 606/213, 151, 606/1, 191–200

[56] References Cited

U.S. PATENT DOCUMENTS

| | | |
|---|---|---|
| 3,874,388 | 4/1975 | King et al. . |
| 4,007,743 | 2/1977 | Blake . |
| 4,665,906 | 5/1987 | Jervis . |
| 4,836,204 | 6/1989 | Landymore et al. . |
| 4,917,089 | 4/1990 | Sideris ..................................... 606/215 |
| 5,067,957 | 11/1991 | Jervis ...................................... 606/108 |
| 5,108,420 | 4/1992 | Marks ...................................... 606/213 |
| 5,171,259 | 12/1992 | Inoue ....................................... 606/213 |
| 5,190,536 | 3/1993 | Jervis ........................................ 606/78 |
| 5,246,445 | 9/1993 | Yachia et al. ............................ 606/108 |
| 5,334,217 | 8/1994 | Das .......................................... 606/213 |
| 5,451,235 | 9/1995 | Lock et al. ............................... 606/213 |
| 5,456,693 | 10/1995 | Conston et al. ......................... 606/192 |
| 5,466,242 | 11/1995 | Mori ........................................ 606/198 |
| 5,522,822 | 6/1996 | Phelps et al. ............................ 606/151 |
| 5,527,338 | 6/1996 | Purdy ...................................... 606/200 |
| 5,597,378 | 1/1997 | Jervis ........................................ 606/78 |
| 5,634,936 | 6/1997 | Linden et al. ........................... 606/213 |
| 5,645,558 | 7/1997 | Horton .................................... 606/191 |
| 5,702,421 | 12/1997 | Schneidt ................................. 606/213 |
| 5,709,707 | 1/1998 | Lock et al. ............................... 606/213 |

FOREIGN PATENT DOCUMENTS 489252  10/1976  Australia .

OTHER PUBLICATIONS

"Catheter Closure of the Ductus Arteriosus" by Lee Benson, M.D.F.R.C.P. (C.)—Transcatheter Therapy in Pediatric Cardiology—pp. 321–3333.

"Transcatheter Closure of Atrial Septal Defects" by Larry A. Latson, M.D.—Transcatheter in Pediatric Cardiology—pp. 335–348.

Transcatheter Closure of Heart Defects: Role of "Buttoned" Devices by P. Syamasundar Rao, M.D., and E.B. Sideris, M.D. Transcatheter Therpy in Pediatric Cardiology—pp. 349–369.

*Primary Examiner*—Michael Buiz
*Assistant Examiner*—Vikki Trinh
*Attorney, Agent, or Firm*—Nikolai, Mersereau & Dietz, P.A.

[57] ABSTRACT

A collapsible medical device and associated method for occluding an abnormal opening in, for example, a body organ, wherein the medical device is shaped from a shape memory metal fabric. The device may be used, for example, to non-surgically treat a patient having a Patent Foramen Ovale (PFO) and resulting paradoxical cerebral emboli. The device is preferably made from a continuous tubular metal fabric and includes two outer occluding portions and a resilient central, spring-like interconnecting member. The metal fabric may be heat treated within a mold in order to substantially set a desired shape of the device. The medical device includes a fastener for attaching to the end of a guide wire or delivery catheter. The medical device having the desired relaxed shape may be collapsed and delivered through a catheter or the like for deployment in a desired channel or opening in a patient's body.

30 Claims, 4 Drawing Sheets

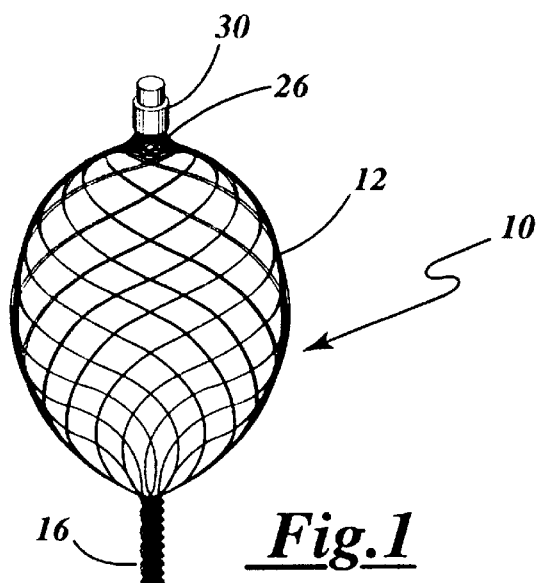
Fig.1
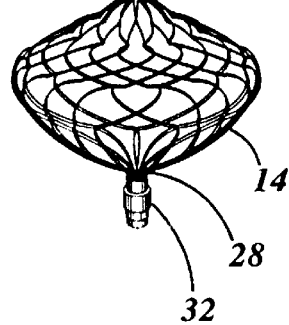
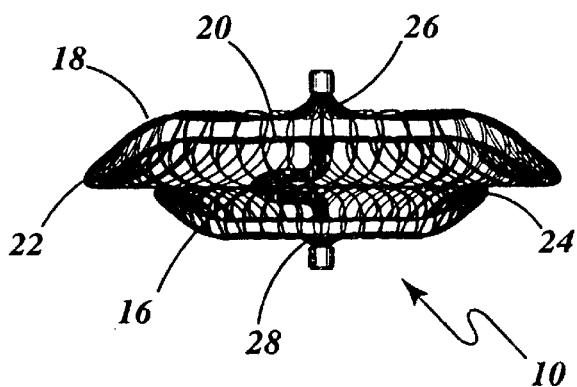
Fig.2
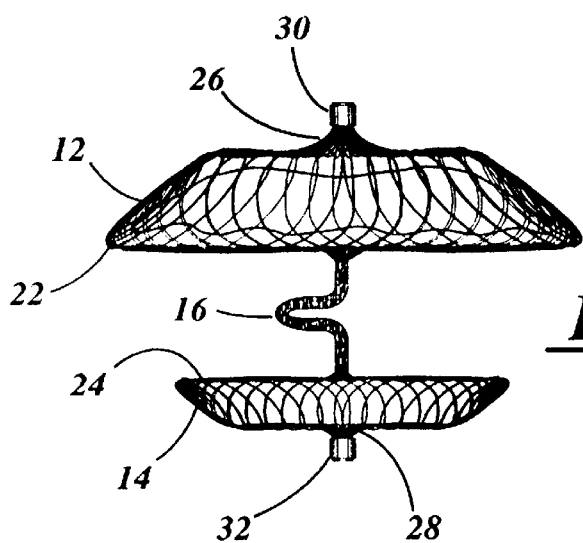
Fig.3

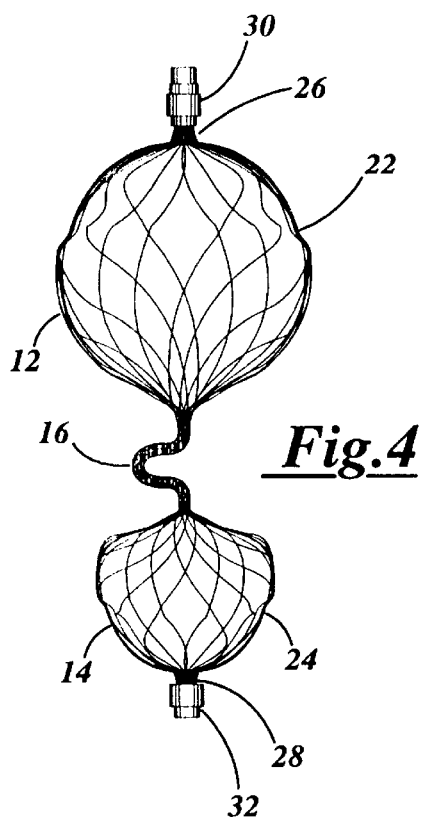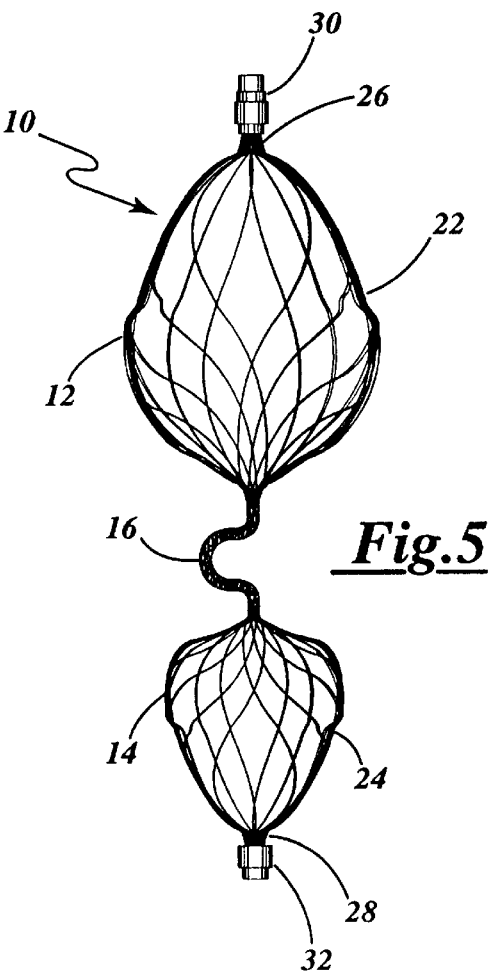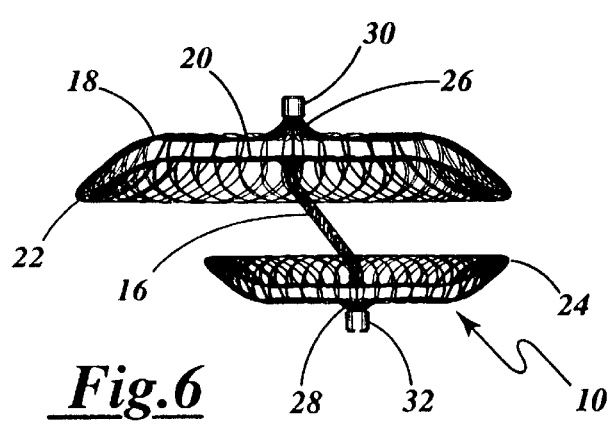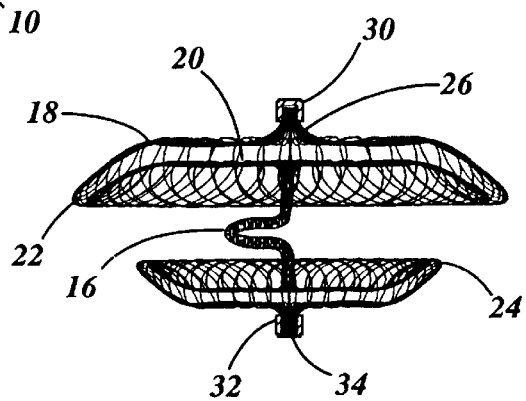

PERCUTANEOUS CATHETER DIRECTED CONSTRICTING OCCLUSION DEVICE

BACKGROUND OF THE INVENTION

I. Field of the Invention

The present invention relates generally to a device and non-surgical method for treating certain cardiac defects. More particularly, the present invention relates to a low profile occlusion device for non-surgical treatment of a patient having a Patent Foramen Ovale (PFO) and resulting paradoxical cerebral emboli. The device made in accordance with the invention is capable of automatically adjusting to a septal defect having eccentric openings and is particularly well suited for delivery through a catheter or the like to a remote location in a patient's heart or in analogous vessel or organ within a patient's body.

II. Description of the Related Art

A wide variety of intra cardiac devices are used in various medical procedures. Certain intravascular devices, such as catheters and guide wires, may be used to deliver fluids or other medical devices to a specific location within a patient's heart. For example, a catheter may be used to reach a selective coronary artery within the vascular system or the catheter and/or guidewire may be used to deliver a device to an interior chamber of the patient's heart. Complex devices may be delivered and used in treating specific abnormal conditions, such as devices used in removing vascular occlusions or devices used in treating septal defects and the like.

Balloon catheters and collapsible preformed polymeric devices similar to that disclosed by Landymore et al. in U.S. Pat. No. 4,836,204 and Linden et al. in U.S. Pat. No. 5,634,936 respectively have been used to occlude a septal defect. When using a balloon catheter similar to that disclosed in the '204 patent, an expandable balloon is carried on a distal end of the catheter. When the catheter is guided to the desired location, the balloon is filled with a fluid until it substantially fills the vessel and becomes lodged therein. Resins which will harden inside the balloon, such as an acrylonitrile, can be employed to permanently fix the size and shape of the balloon. The balloon can then be detached from the end of the catheter and left in place. The '936 device is expanded and hardened by a ternary system that modifies the pH and hydrophilicity of the device (see '936 patent, col. 6, ln 40–45). If these devices are not expanded completely they may not firmly lodge in the septal defect and may rotate and loosen from the septal wall, thereby releasing into the blood stream. Overfilling the '204 device is an equally undesirable occurrence which may lead to the rupture of the balloon and release of resins into the patient's bloodstream.

Mechanical embolization devices have been proposed in the past for occluding defects in a patient's intravascular system. The devices typically include a pair of spaced apart patches each having an internal collapsible frame (similar to the frame and outer membrane of an umbrella), wherein the opposing patch and frame are interconnected by a conjoint member. The patches are typically aligned and attached to a common axis of the conjoint member. The conjoint member may be a rigid or semi-rigid hub which minimizes the movement of the patches both laterally and fore and aft to thereby firmly retain the patches against the septal wall adjacent the defect. Patches that are attached to a common axis of the hub may become problematic when the septal defect to be occluded has eccentric openings. Since the patches are attached to a common rigid axis, at least one of the eccentric openings may not be completely covered by the respective patch. The rigid or semi-rigid hub prevents adjustment of the patches to compensate for the eccentric openings.

Representative examples of such mechanical devices are disclosed in King et al., U.S. Pat. No. 3,874,388 (the '388 patent), Das, U.S. Pat. No. 5,334,217 (the '217 patent), European application No. 0541,063 A2 (the '063 application), Sideris, U.S. Pat. No. 4,917,089 (the '089 patent), and Marks, U.S. Pat. No. 5,108,420 (the '420 patent). These devices are typically pre-loaded into an introducer or delivery catheter prior to the implantation procedure and are not commonly loaded by the physician during the medical procedure. During deployment of these devices, recapture into the delivery catheter is difficult if not impossible, thereby limiting the effectiveness of these devices.

Prior to implantation of these devices, the thickness of the septal wall near the defect and the approximate width of the defect must be determined in order that an appropriately sized device may be provided. A balloon catheter and a calibrated guidewire having radiopaque regions of known length, may be utilized by a physician during a preliminary fluoroscopic procedure to estimate the defect's size, shape and thickness of the septal wall near the defect. Although useful, the defects exact size and shape cannot be determined, thereby increasing the possibility of leakage around the occluding device. Hence, a device that inherently adjusts to the shape and thickness of the defect would be desirable.

Significantly, the size of the prior devices is inherently limited by the structure and form of the device. Also, when using occluding devices such as those disclosed in the '089, '388, '217, or '420 patents to occlude a septal defect, the pressure and therefore the chance of dislodgment of the device increases with an increase in size of the defect. Consequently, the prior devices require an oversized retention skirt positioned on each side of the defect. Oftentimes, the position of the septal defect dictates the size of the retention skirt. In a membranous type septal defect, it is difficult if not improbable to be able to effectively position the '388, '217, '089, or '420 device without at least partially closing off the aorta. Also, these disclosed devices tend to be rather expensive and time-consuming to manufacture.

Further, the shape of the prior devices (for example squares, triangles, pentagons, hexagons and octagons) require a larger surface contact area and have corners which may extend to the free wall of the atria. Each time the atria contracts (approximately 100,000 times per day) the corners extending to the atria walls are bent, creating structural fatigue fractures in approximately 30 percent of all cases. Furthermore, the previous devices require a French 14–16 introducing catheter, making it impossible to treat children affected with congenital defects with these devices. Hence, it would be advantageous to provide a reliable embolization device which is both easy to deploy through a 6–7 French catheter and which automatically adjusts to the shape and thickness of the defect. The present invention addresses these and other disadvantages of the prior art.

SUMMARY OF THE INVENTION

It is accordingly a principal object of the present invention to provide a reliable, low-profile, intra cardiac occlusion device capable of automatically adjusting the alignment within a septal defect having eccentric openings, wherein the device is suitable for treating septal defects including a Patent Foramen Ovale (PFO). PFO is essentially a condition wherein an abnormal, wide, opening is present in the septal wall between the two atria of the heart. Blood can flow directly between these two atria, compromising the normal flow of blood and efficiency of the patient's heart. The abnormal opening or septal defect may not extend perpendicularly through the septal wall. Rather, the center of the opening in the septal wall in the left atrium may be eccentric to the center of the opening in the septal wall in the right atrium, thereby requiring eccentric positioned "patches" to effectively occlude the defect. Also, the septal wall may be very thin requiring a minimal separation distance between the two occluding "patches". The device of the present invention is preferably formed from a continuous tubular metal fabric and includes two opposing spaced apart "discs", patches, or retention skirts interconnected by a flexible or resilient central member. The central member flexes both laterally and in the fore and aft directions while providing an inward tension against each of the discs.

When forming these intravascular devices from a resilient metal fabric a plurality of resilient strands or wires are provided, with the metal fabric being formed by braiding the resilient strands to create a resilient material. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines a relaxed state of a medical device which can be stretched or expanded and deployed through a catheter into a channel in a patient's body. Those skilled in the art will appreciate that the cavities of the molds must mirror the desired shape of the device and further molding elements are described in co-pending application Ser. No. 08/647,712 filed on May 14, 1996, and entitled PERCUTANEOUS CATHETER DIRECTED INTRAVASCULAR OCCLUSION DEVICE which is assigned to the same assignee as the present invention, the entire disclosure of which is incorporated herein by reference.

The device of the present invention has a specific shape which is particularly well suited for occluding a PFO. The device has a relaxed low-profile configuration and includes clamps that allow attachment of the device to an end of a delivery device or guide wire (allowing recovery of the device after placement). In use, a guide catheter is positioned and advanced in a patient's body such that the distal end of the catheter is adjacent a desired treatment site for treating a physiological condition. The medical device of the present invention having a predetermined shape is then stretched and inserted into the lumen of the catheter. The device is urged through the catheter and out the distal end, whereupon, due to its shape memory property it will tend to substantially return to its relaxed state adjacent the treatment site. The guide wire or delivery catheter is then released from the clamp and removed.

OBJECTS

It is accordingly a principal object of the present invention to provide a device suitable for occluding a septal defect that is capable of automatically adjusting to eccentric openings of the septal defect while providing an inward tension on the occluding portions of the device.

Another object of the present invention is to provide a device suitable for occluding septal defects having eccentric openings, wherein the device is particularly well suited for delivery through a catheter or the like to a remote location in a patient's heart or in an analogous vessel or organ within a patient's body.

A further object of the present invention is to provide an occluding device having outer occluding portions and a flexible resilient central portion that pulls the outer occluding portions together.

These and other objects, as well as these and other features and advantages of the present invention will become readily apparent to those skilled in the art from a review of the following detailed description of the preferred embodiment in conjunction with the accompanying claims and drawings in which like numerals in the several views refer to corresponding parts.

BRIEF DESCRIPTION OF THE DRAWINGS

FIG. 1 is a perspective view of a Patent Foramen Ovale occluding device in accordance with the present invention;

FIG. 2 is a side elevational view of the medical device of the type shown in FIG. 1;

FIG. 3 is a partial sectional side elevational view of the medical device of the type shown in FIG. 2, shown partially stretched along its longitudinal axis;

FIG. 4 is a side elevational view of the medical device of the type shown in FIG. 3, shown stretched along its longitudinal axis slightly more than in FIG. 3;

FIG. 5 is a side elevational view of the medical device of the type shown in FIG. 4, shown stretched along its longitudinal axis slightly more than in FIG. 4;

FIG. 6 is a side elevational view of the medical device of the type shown in FIG. 1 shown partially stretched, wherein the outer perimeter of the spaced apart discs are offset;

FIG. 7 is a partial sectional side elevational view of the medical device of the type shown in FIG. 1, shown partially stretched along its longitudinal axis;

DETAILED DESCRIPTION OF THE PREFERRED EMBODIMENT

Figure 11:
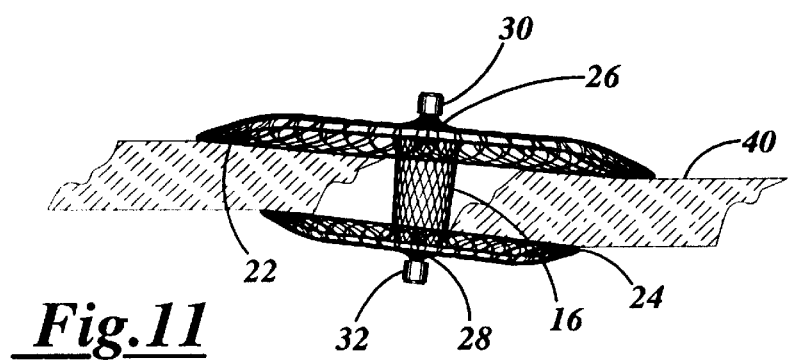
FIG. 11 is a partial sectional side elevational view of the embodiment of FIG. 8 shown occluding a PFO of the septal wall.
Figure 12:
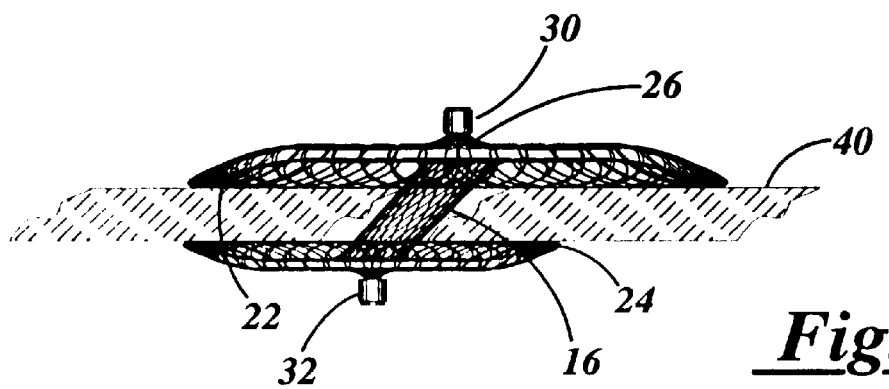
FIG. 12 is a partial sectional side elevational view of the embodiment of FIG. 8 shown occluding a PFO of the septal wall.
Figure 13:
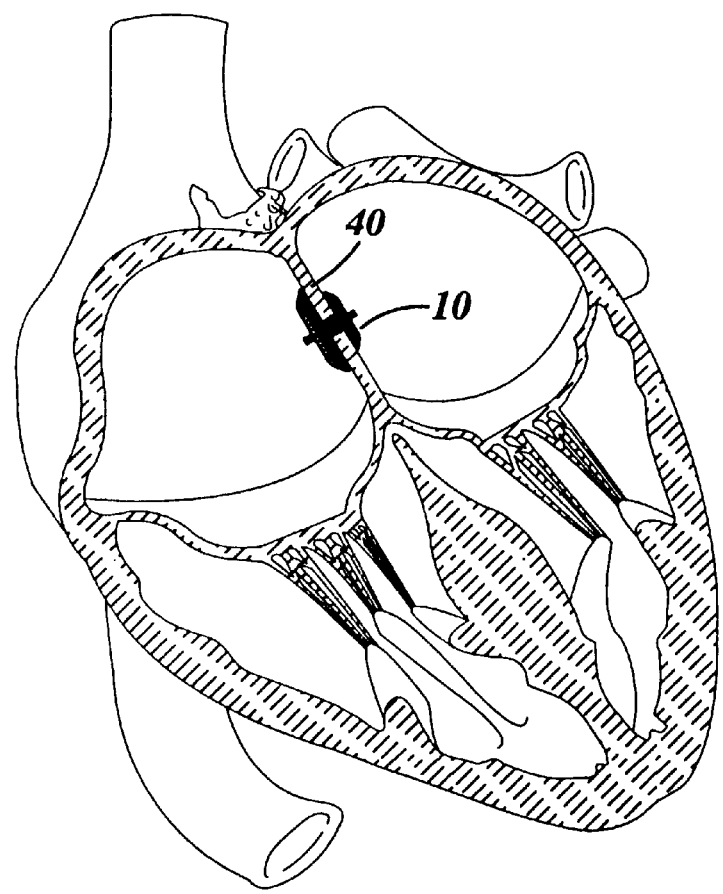
FIG. 13 is a partial sectional side elevational view of the embodiment of FIG. 1 shown occluding an atrial septal defect.

The present invention provides a percutaneous catheter directed occlusion device for use in occluding an abnormal opening in a patient's body that is particularly well suited for occluding a PFO (see FIGS. 11–13). The occluding device includes two spaced apart occluding members interconnected by a flexible, resilient center portion. A clamp is attached to an outer end of each occluding member, wherein the clamps are adapted for coupling to the end of a guidewire or catheter for delivery to a pre-selected site within the patient. In the preferred embodiment, the occluding device is formed from a single continuous tubular metal fabric.

The tubular fabric is formed from a plurality of wire strands having a predetermined relative orientation between the strands. Those skilled in the art will appreciate that the pick and pitch of the braided wires may be varied depending upon the desired density of the fabric. The tubular fabric has metal strands which define two sets of essentially parallel generally spiraling and overlapping strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. the number of turns per unit length) as well as some other factors, such as the number of wires employed in a tubular braid, the size or diameter of each wire in the braid, and the diameter of the braid are all important in determining a number of important properties of the device. For example, the greater the pick and pitch of the fabric, and hence the greater the density of the wire strands in the fabric, the stiffer the device will be. Also, the greater the diameter of each wire of the braid, the stiffer the device will be. Having a greater wire density will also provide the device with a greater wire surface area, which will generally enhance the tendency of the device to occlude the area in which it is deployed. This thrombogenicity can be either enhanced by a coating of a thrombolytic agent, or abated by a coating of a lubricious, anti-thrombogenic compound. When using a tubular braid to form a device of the present invention, a tubular braid of about 4 mm in diameter having approximately 72 braided wires is suitable for fabricating devices capable of occluding abnormal openings and/or septal defects.

The wire strands of the tubular metal fabric are preferably manufactured from so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

Without any limitation intended, suitable wire strand materials may be selected from a group consisting of a cobalt-based low thermal expansion alloy referred to in the field as ELGELOY, nickel-based high temperature high-strength "superalloys" (including nitinol) commercially available from, for example, Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface (as described below) when subjected to a predetermined heat treatment.

In the preferred embodiment, the wire strands are made from a shape memory alloy, NiTi (known as nitinol) which is an approximately stoichiometric alloy of nickel and titanium and may also include other minor amounts of other metals to achieve desired properties. Handling requirements and variations of NiTi alloy composition are known in the art, and therefore such alloys need not be discussed in detail here. U.S. Pat. No. 5,067,489 (Lind) and 4,991,602 (Amplatz et al.), the teachings of which are incorporated herein by reference, discuss the use of shape memory NiTi alloys in guide wires. Such NiTi alloys are preferred, at least in part, because they are commercially available and more is known about handling such alloys than other known shape memory alloys. NiTi alloys are also very elastic and are said to be "super elastic" or "pseudo elastic". This elasticity allows a device of the invention to return to a preset configuration after deployment.

When forming a medical device in accordance with the present invention, an appropriately sized piece of tubular metal fabric is inserted into a mold, whereby the fabric deforms to generally conform to the shape of the cavities within the mold. The shape of the cavities are such that the metal fabric deforms into substantially the shape of the desired medical device. Cores within the cavities may be used to further form the shape of the fabric within the cavities. The ends of the wire strands of the tubular metal fabric should be secured to prevent the metal fabric from unraveling. A clamp or welding, as further described below, may be used to secure the ends of the wire strands.

During the molding procedure, a molding element may be positioned within the lumen of the tubular braid prior to insertion into the mold to thereby further define the molding surface. If the ends of the tubular metal fabric have already been fixed by a clamp or welding, the molding element may be inserted into the lumen by manually moving the wire strands of the fabric apart and inserting the molding element into the lumen of the tubular fabric. By using such a molding element, the dimensions and shape of the finished medical device can be fairly accurately controlled and ensures that the fabric conforms to the mold cavity.

The molding element may be formed of a material selected to allow the molding element to be destroyed or removed from the interior of the metal fabric. For example, the molding element may be formed of a brittle or friable material. Once the material has been heat treated in contact with the mold cavities and molding element, the molding element can be broken into smaller pieces which can be readily removed from within the metal fabric. If this material is glass, for example, the molding element and the metal fabric can be struck against a hard surface, causing the glass to shatter. The glass shards can then be removed from the enclosure of the metal fabric.

Alternatively, the molding element can be formed of a material that can be chemically dissolved, or otherwise broken down, by a chemical agent which will not substantially adversely affect the properties of the metal wire strands. For example, the molding element can be formed of a temperature resistant plastic resin which is capable of being dissolved with a suitable organic solvent. In this instance, the metal fabric and the molding element can be subjected to a heat treatment to substantially set the shape of the fabric in conformance with the mold cavity and molding element, whereupon the molding element and the metal fabric can be emersed in the solvent. Once the molding element is substantially dissolved, the metal fabric can be removed from the solvent.

Care should be taken to ensure that the materials selected to form the molding element are capable of withstanding the heat treatment without losing its shape, at least until the shape of the fabric has been set. For example, the molding element could be formed of a material having a melting point above the temperature necessary to set the shape of the wire strands, but below the melting point of the metal forming the strands. The molding element and metal fabric could then be heat treated to set the shape of the metal fabric, whereupon the temperature would be increased to substantially completely melt the molding element, thereby removing the molding element from within the metal fabric.

Those skilled in the art will appreciate that the specific shape of the molding element produces a specific shape of the molded device. If a more complex shape is desired, the molding element and mold may have additional parts including a camming arrangement, but if a simpler shape is being formed, the mold may have few parts. The number of parts in a given mold and the shapes of those parts will be dictated almost entirely by the shape of the desired medical device to which the metal fabric will generally conform.

When the tubular braid, for example, is in its preformed relaxed configuration, the wire strands forming the tubular braid will have a first predetermined relative orientation with respect to one another. As the tubular braid is compressed along its axis, the fabric will tend to flare out away from the axis conforming to the shape of the mold. When the fabric is so deformed the relative orientation of the wire strands of the metal fabric will change. When the mold is assembled, the metal fabric will generally conform to the molding surface of the interior cavity. After undergoing the shape memory process, the resulting medical device has a preset relaxed configuration and a collapsed or stretched configuration which allows the device to be passed through a catheter or other similar delivery device. The relaxed configuration is generally defined by the shape of the fabric when it is deformed to generally to conform to the molding surface of the mold.

Once the tubular or planar metal fabric is properly positioned within a preselected mold with the metal fabric generally conforming to the molding surface of the cavities therein, the fabric can be subjected to a heat treatment while it remains in contact with the molding surface. Suitable heat treatment processing of nitinol wire to set a desired shape are well known in the art. Spirally wound nitinol coils, for example, are used in a number of medical devices, such as in forming the coils commonly carried around distal links of guide wires. A wide body of knowledge exists for forming nitinol in such devices, so there is no need to go into great detail here on the parameters of a heat treatment for the nitinol fabric preferred for use in the present invention. Briefly, though, it has been found that holding a nitinol fabric at about 500 degrees centigrade to about 550 degrees centigrade for a period of about 1 to 30 minutes, depending upon the softness or hardness of the device to be made will tend to set the fabric in its deformed state, i.e., wherein it conforms to the molding surface of the mold cavities. At lower temperatures, the heat treatment time will tend to be greater (e.g., about 1 hour at about 350 degrees centigrade) and at higher temperatures the time will tend to be shorter (e.g., about 30 seconds at about 900 degrees centigrade). These parameters can be varied as necessary to accommodate variations in the exact composition of the nitinol, prior heat treatment of the nitinol, the desired properties of the nitinol in the finished article, and other factors known to those skilled in this field.

Instead of relying on convection heating or the like, it is also known in the art to apply an electrical current to the nitinol to heat it. In the present invention, this can be accomplished by, for example, connecting electrodes to each end of the metal fabric. The wire can then be heated by resistance heating of the wires in order to achieve the desired heat treatment, which will tend to eliminate the need to heat the entire mold to the desired heat treating temperature in order to heat the metal fabric to the desired temperature. The materials, molding elements and methods of molding a medical device from a tubular or planar metal fabric is further described in co-pending U.S. patent application Ser. No. 08/647,712, filed May 14, 1996 and assigned to the same assignee as the present invention, the entire disclosure of which is incorporated herein by reference.

Heat treating the metal fabric at temperatures ranging between 500–550 degrees centigrade substantially sets the shapes of the wire strands in a reoriented relative position conforming the shape of the fabric to the molding surface. When the metal fabric is removed from the mold, the fabric maintains the shape of the molding surfaces of the mold cavities to thereby define a medical device having a desired shape. After the heat treatment, the fabric is removed from contact with the molding cavity and will substantially retain its shape in a deformed state. If a molding element is used, this molding element can be removed as described above.

The time required for the heat treating process will depend in large part upon the material of which the wire strands of the metal fabric are formed and mass of the mold, but the time and temperature of the heat treatment should be selected to substantially set the fabric in its deformed state, i.e., wherein the wire strands are in their reoriented relative configuration and the fabric generally conforms to the molding surface. The required time and temperature of the heat treatment can vary greatly depending upon the material used in forming the wire strands. As noted above, one preferred class of materials for forming the wire strands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a super elastic or pseudo elastic phase. By heating the nitinol above a certain phase transition temperature, the crystal structure of the nitinol metal will tend to "set" the shape of the fabric and the relative configuration of the wire strands in the positions in which they are held during the heat treatment.

Once a device having a preselected shape has been formed, the device may be used to treat a physiological condition of a patient. A medical device suitable for treating the condition is selected. Once the appropriate medical device is selected, a catheter or other suitable delivery device may be positioned within a channel in a patient's body to place the distal end of the delivery device adjacent the desired treatment cite, such as immediately adjacent (or even within) the shunt of an abnormal opening in the patient's organ for example.

The delivery device (not shown) can take any suitable shape, but desirably comprises an elongate flexible metal shaft having a threaded distal end. The delivery device can be used to urge the medical device through the lumen of a catheter for deployment in a channel of a patient's body. When the device is deployed out the distal end of the catheter, the device will still be retained by the delivery device. Once the medical device is properly positioned within the shunt of the abnormal opening, the distal end of the catheter may be pressed against the medical device and the metal shaft or guidewire can be rotated about its axis to unscrew the medical device from the threaded distal end of the shaft. The catheter and guidewire are then withdrawn.

By keeping the medical device attached to the delivery means, the operator can retract the device for repositioning relative to the abnormal opening, if it is determined that the device is not properly positioned within the shunt. A threaded clamp attached to the medical device allows the operator to control the manner in which the medical device is deployed out the distal end of the catheter. When the device exits the catheter, it will tend to resiliently return to a preferred relaxed shape. When the device springs back into this shape, it may tend to act against the distal end of the catheter effectively urging itself forward beyond the end of the catheter. This spring action could conceivably result in improper positioning of the device if the location of the device within a channel is critical, such as where it is being positioned in a shunt between two vessels. Since the threaded clamp can enable the operator to maintain a hold on the device during deployment, the spring action of the device can be controlled by the operator to ensure proper positioning during deployment.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the PFO occluding device may have a relatively elongated collapsed configuration wherein the device is stretched along its longitudinal axis (see FIG. 5). This collapsed configuration can be achieved simply by stretching the device generally along its axis, e.g. by manually grasping the clamps and pulling them apart, which will tend to collapse the relaxed diameter portions of the device inwardly toward the device's axis. Loading such a device into a catheter may be done at the time of implantation and does not require pre-loading of the introducer or catheter.

If the device is to be used to permanently occlude a channel in the patient's body, one can simply retract the catheter and remove it from the patient's body. This leaves the medical device deployed in the patient's vascular system so that it may occlude the blood vessel or other channel in the patient's body. In some circumstances, the medical device may be attached to a delivery system in such a manner as to secure the device to the end of the delivery means. Before removing the catheter in such a system, it may be necessary to detach the medical device from the delivery means before removing the catheter and the delivery means.

When the device is deployed in a patient, thrombi will tend to collect on the surface of the wires. By having a greater wire density, the total surface area of the wires will be increased, increasing the thrombotic activity of the device and permitting it to relatively rapidly occlude the vessel in which it is deployed. It is believed that forming the occlusion device from a 4 mm diameter tubular braid having a pick of at least about 40 and a pitch of at least about 30° will provide sufficient surface area to substantially completely occlude an abnormal opening in the septal wall. If it is desired to increase the rate at which the device occludes, any of a wide variety of known thrombotic agents can be applied to the device. Those skilled in the art will appreciate that an occluding membrane, fiber, or mesh may be positioned within either or both discs 12 and 14 to further enhance the occluding feature of each disc (see FIG. 3).

Having described the details of the invention, specific reference to the Figures will next be presented. The several Figures illustrate several embodiments of the invention wherein the central portion is resilient and pulls the outer discs towards each other. Referring first to the FIGS. 1 and 2, there is shown generally the device 10 suitable for occluding a Patent Foramen Ovale (PFO). In its relaxed, unstretched state (see FIG. 2), the device 10 generally includes two aligned discs 12 and 14 linked together by a resilient central portion 16. The plurality of braided wires form an outer 18 and inner 20 surface of each disc. The inner surface 20 of each disc may be concave or cupped (see also FIG. 7) to ensure that the outer perimeter edge 22 and 24 of each disc 12 and 14 respective contacts the septal wall 40.

When the device 10 is in a relaxed state, the discs 12 and 14 tend to overlap and the central portion 16 extends into the recess formed by the inner surface of the discs 12 and 14. In this manner, when the discs 12 and 14 are pulled apart (see FIG. 3) the spring-like action of the central portion 16 will cause the perimeter edge 22 and 24 of the corresponding disc to fully engage the sidewall of the septum (see FIGS. 11 and 12). FIGS. 3–5 illustrates sequentially the stretching, spring-like action of the bent central portion 16. Without any limitation intended, during the formation of the device 10, the tubular braid (in the region forming the central portion 16) is partially flattened to enhance the spring-like action of the central portion 16. FIG. 6 illustrates that the discs 12 and 14 may be offset laterally by stretching the central portion 16.

The ends 26 and 28 of the tubular braided metal fabric device 10 are welded or clamped together with corresponding clamps 30 and 32 to avoid fraying. Of course the ends may alternately be held together by other means readily known to those skilled in the art. Further, it is to be understood that other suitable fastening means may be attached to the ends 26 and 28 in other ways, such as by welding, soldering, brazing, use of biocompatible cementious material or in any other suitable fashion. The clamps 30 and 32 tying together the wire strands at corresponding ends 26 and 28 also serve to connect the device to a delivery system. In the embodiment shown, the clamps 30 and 32 are generally cylindrical in shape and have a threaded bore 34 (see FIG. 7) for receiving the ends 26 and 28 of the metal fabric to substantially prevent the wires from moving relative to one another. The threaded bore 34 is adapted to receive and engage a threaded distal end of a delivery device.

Figure 8:
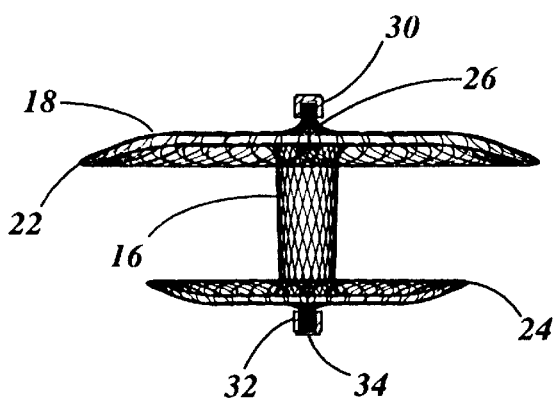
FIG. 8 is a side elevational view of another embodiment of the present invention shown partially stretched along its longitudinal axis.
Figure 9:
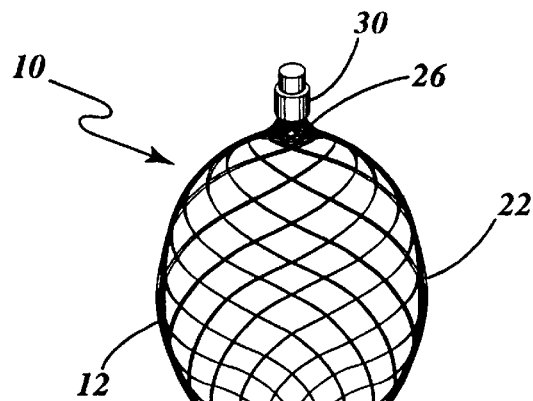
FIG. 9 is a side elevational view of another embodiment of the present invention shown partially stretched along its longitudinal axis.
Figure 10:
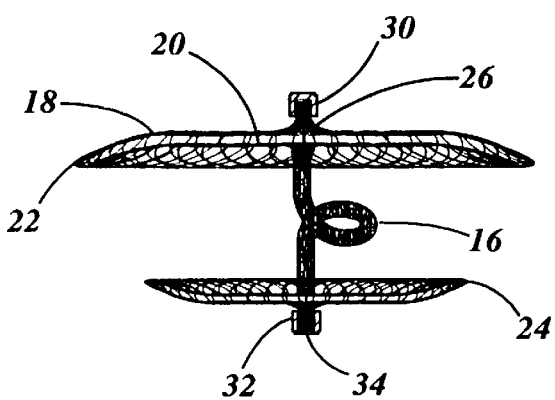
FIG. 10 is a side elevational view of another embodiment of the present invention shown partially stretched along its longitudinal axis.

FIGS. 8–10 show additional embodiments of the device 10 wherein the shape of the resilient central portion 16 is varied. The central portion 16 is flexible in both the lateral and fore and aft directions. This flexibility provides a self centering feature of the device, wherein the discs 12 and 14 tend to automatically center themselves around the adjacent opening of the defect (see FIGS. 11 and 12) while tending to pull the discs toward the other. The central portion 16 may include a helical spring-like shape (see FIG. 9), a coil shape (see FIG. 10), or a bent shape (see FIG. 2).

Those skilled in the art will appreciate that the device 10 is sized in proportion to the shunt to be occluded. The diameter of each disc 12 and 14 may be varied as desired for differently sized openings in the septal wall. Further, the length of the resilient central portion may be varied depending upon the thickness of the septal wall, and may range between 4 to 40 mm.

The PFO occlusion device 10 can advantageously be made in accordance with the method outlined above. The device is preferably made from a 0.005 inch nitinol wire mesh. The braiding of the wire mesh may be carried out with 28 picks per inch at a shield angle of about 64 degrees using a Maypole braider with 72 wire carriers. The stiffness of the PFO device 10 may be increased or decreased by altering the wire size, the shield angle, the pick size, braid diameter, the number of wire carriers, or the heat treatment process. Those skilled in the art will recognize from the preceding discussion that the cavities of a mold must be shaped consistent with the desired shape of the PFO device.

When using untreated NiTi fabrics, the strands will tend to return to their unbraided configuration and the braid can unravel fairly quickly unless the ends of the length of the braid are constrained relative to one another. The clamps 30 and 32 are useful to prevent the braid from unraveling at either end, thereby effectively defining an empty space within a sealed length of fabric. These clamps 30 and 32 hold the ends of the cut braid together and prevent the braid from unraveling. Although soldering and brazing of NiTi alloys has proven to be fairly difficult, the ends may be welded together, such as by spot welding with a laser welder. When cutting the fabric to the desired dimensions, care should be taken to ensure that the fabric will not unravel. In the case of tubular braids formed of NiTi alloys, for example, the individual strands will tend to return to their heat set configuration unless constrained. If the braid is heat treated to set the strands in the braided configuration, they will tend to remain in the braided form and only the ends will become frayed. However, it may be more economical to simply form the braid without heat treating the braid since the fabric will be heat treated again in forming the medical device.

Use of a device 10 of the present invention will now be discussed in greater detail with respect to occluding a PFO. The device may be delivered and properly placed using two dimensional echocardiography and Doppler color flow mapping. As indicated above, the delivery device can take any suitable shape, preferably comprising an elongated flexible metal shaft similar to a conventional guide wire. The delivery device is used to advance the PFO occlusion device through the lumen of a small diameter cylindrical tube, such as a delivery catheter, for deployment. The PFO device 10 is loaded into the small diameter cylindrical tube by using a loading sheath to stretch the device and put the same in an elongated or stretched condition. The device may be inserted into the lumen of the tube during the procedure or preassembled at a manufacturing facility, in that the devices of the present invention do not take on a permanent set when maintained in a compressed state.

From a femoral vein approach, the delivery catheter or tube is passed across the PFO. The device 10 is advanced through the delivery catheter until the distal end becomes unconstrained on exiting the end of the catheter, whereupon it assumes its disc-like shape in the left atrium (see FIG. 13). The delivery catheter is then pulled back in the proximal direction across the PFO and the delivery device is likewise pulled in a proximal direction, urging the distal disc against the septum. The delivery catheter is then further pulled away from the septum, allowing the proximal disc to extend out of the delivery catheter, where it resiliently returns to its predefined relaxed disc-like shape. In this manner, the PFO device is positioned such that the distal disc presses against one side of the septum while the proximal disc presses against the other side of the septum. In order to increase its occluding ability, the device can contain polyester fibers or a nylon fabric (see FIG. 3). In instances where the device is improperly deployed on a first try, the device may be recovered by pulling the delivery device proximally, thereby retracting the device 10 back into the delivery catheter prior to a second attempt at positioning the device relative to the defect.

When the PFO occluding device is properly placed, the physician rotates the guidewire, unscrewing the threaded distal end of the guidewire from the clamp 30 or 32 of the occluding device 10. The threads on the clamp are such that the rotation of the guidewire unscrews the guidewire from the clamp of the occluding device 10, rather than merely rotating the occluding device. As noted above, the threaded clamp can also enable the operator to maintain a hold on the device during deployment, or enables the operator to control the spring action during deployment of the device to ensure proper positioning.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself

What is claimed is:

1. A collapsible medical device, comprising a metal fabric including a plurality of woven metal strands having a proximal end and a distal end, each end having means for securing the metal fabric attached thereto, thereby inhibiting unraveling of the metal fabric, said metal fabric having a relaxed configuration having two enlarged diameter portions and a central portion disposed between the two enlarged diameter portions wherein said central portion allows lateral movement of each of said two enlarged diameter portions with respect to the other, said device further having a collapsed configuration for delivery through a channel in a patient's body.

2. The device as recited in claim 1, wherein each enlarged diameter portion has an inner and outer wall such that the inner wall of at least one of the enlarged diameter portions is at least partially concave.

3. The device as recited in claim 1, wherein said central portion is shaped to form a resilient portion to thereby pull the two enlarged diameter portions toward the other.

4. The device as recited in claim 1, wherein said central portion is helically shaped to form a resilient portion to thereby pull the two enlarged diameter portions toward the other.

5. The device as recited in claim 1, wherein said central portion is coiled to form a resilient portion to thereby pull the two enlarged diameter portions toward the other.

6. The device as recited in claim 1, wherein said central portion is bent to form a resilient portion to thereby pull the two enlarged diameter portions toward the other.

7. The device as recited in claim 2, wherein said central portion is shaped to form a resilient portion to thereby pull the two enlarged diameter portions toward the other.

8. The device as recited in claim 1, wherein a separation distance between the two enlarged diameter portions is less than a thickness of a patient's atrial septum.

9. The medical device as recited in claim 1, wherein an inner surface of a first enlarged diameter portion is at least partially concave and a length of the central portion is dimensioned such that a perimeter edge of the first enlarged diameter portion overlaps a perimeter edge of a second enlarged diameter portion.

10. The medical device as recited in claim 1, said two enlarged diameter portions consisting of a first enlarged partially concave diameter portion and a second enlarged partially concave diameter portion.

11. The medical device as recited in claim 1, said two enlarged diameter portions consisting of a first enlarged diameter portion and a second enlarged diameter portion, wherein the central portion may be flexed such that a first central axis of the first enlarged diameter portion is offset from a second central axis of the second enlarged diameter portion.

12. The medical device as recited in claim 1, wherein said means for securing includes means for attachment to a delivery device.

13. A collapsible medical device, comprising a metal fabric including a plurality of woven metal strands having a proximal end and a distal end, each end having means for securing the metal fabric attached thereto, thereby inhibiting unraveling of the metal fabric, said metal fabric having a relaxed configuration having two enlarged diameter portions and a resilient portion disposed between the two enlarged diameter portions wherein said resilient portion allows lateral movement of each of said two enlarged diameter portions with respect to the other, said device further having a collapsed configuration for delivery through a channel in a patient's body.

14. The device as recited in claim 13, wherein each enlarged diameter portion has an inner and outer wall such that the inner wall of at least one of the enlarged diameter portions is at least partially concave.

15. The device as recited in claim 13, wherein said resilient portion is shaped to thereby pull the two enlarged diameter portions toward the other.

16. The device as recited in claim 13, wherein said resilient portion is helically shaped to thereby pull the two enlarged diameter portions toward the other.

17. The device as recited in claim 13, wherein said resilient portion is coiled to thereby pull the two enlarged diameter portions toward the other.

18. The device as recited in claim 13, wherein said resilient portion is bent to thereby pull the two enlarged diameter portions toward the other.

19. The medical device as recited in claim 13, said two enlarged diameter portions consisting of a first enlarged diameter portion and a second enlarged diameter portion, wherein the resilient portion may be flexed such that a first central axis of the first enlarged diameter portion is offset from a second central axis of the second enlarged diameter portion.

20. A collapsible medical device, comprising two enlarged diameter portions and a flexible central portion interconnecting the two enlarged diameter portions wherein said flexible central portion allows lateral movement of each of said two enlarged diameter portions with respect to the other, said device having a proximal end and a distal end, wherein at least one of the proximal and distal end includes means for securing said device to a delivery system, said device having a collapsed configuration for delivery through a channel in a patient's body.

21. The device as recited in claim 20, wherein said device is formed from a metal fabric consisting of a plurality of woven metal strands.

22. The device as recited in claim 20, wherein each enlarged diameter portion has an inner and outer wall such that the inner wall of at least one of the enlarged diameter portions is at least partially concave.

23. The device as recited in claim 20, wherein said flexible central portion is shaped to form a resilient portion to thereby pull the two enlarged diameter portions toward the other.

24. The device as recited in claim 21, wherein said flexible central portion is shaped to form a resilient portion to thereby pull the two enlarged diameter portions toward the other.

25. The device as recited in claim 20, wherein a separation distance between the two enlarged diameter portions is less than a thickness of a patient's atrial septum.

26. The medical device as recited in claim 20, wherein an inner surface of a first enlarged diameter portion is at least partially concave and a length of the flexible central portion is dimensioned such that a perimeter edge of the first enlarged diameter portion overlaps a perimeter edge of a second enlarged diameter portion.

27. The medical device as recited in claim 20, wherein said means for securing includes means for attachment to a delivery device.

28. The medical device as recited in claim 1, wherein the flexible central portion is shaped to form a stretchable portion, and further wherein the flexible central portion stretches to adjust to a thickness of a patient's atrial septum while the two enlarged diameter portions remain in the relaxed configuration.

29. The medical device as recited in claim 13, wherein the resilient portion is shaped to form a stretchable portion, and further wherein the resilient portion stretches to adjust to a thickness of a patient's atrial septum while the two enlarged diameter portions remain in the relaxed configuration.

30. The medical device as recited in claim 20, wherein the flexible central portion is shaped to form a stretchable portion, wherein the flexible central portion stretches to adjust to a thickness of a patient's atrial septum while the two enlarged diameter portions remain in a preset configuration.

\* \* \* \* \*